United States Patent [19]
Gatzlaff et al.

[11] Patent Number: 5,508,622
[45] Date of Patent: Apr. 16, 1996

[54] COATING DEFECT DETECTOR SYSTEM

[76] Inventors: Harold Gatzlaff, 4545 - 200th St. East, Prior Lake, Minn. 55372; William E. Post, 708 Meadow Ridge NW., Canton, Ohio 44708

[21] Appl. No.: 355,834

[22] Filed: Dec. 14, 1994

[51] Int. Cl.$^6$ ........................................... G01L 5/20
[52] U.S. Cl. ............................ 324/558; 324/701; 324/554; 73/159
[58] Field of Search ................................... 324/558, 544, 324/701, 515, 517; 73/159

[56] References Cited

U.S. PATENT DOCUMENTS

| | | | |
|---|---|---|---|
| 2,220,489 | 11/1940 | Lowkrantz | 324/554 |
| 2,246,906 | 6/1941 | Viebahn et al. | |
| 2,576,043 | 11/1951 | Rendel | |
| 2,930,228 | 3/1960 | Lawrence et al. | |
| 3,042,861 | 7/1962 | Brys | 324/701 |
| 3,188,478 | 6/1965 | Binks | |
| 3,500,437 | 3/1970 | Foerster | |
| 3,633,211 | 1/1972 | Batzdorff | |
| 3,759,095 | 9/1973 | Short, Jr. et al. | |
| 4,351,263 | 9/1982 | Rarig | 324/558 |
| 4,404,634 | 9/1983 | Bautz | 73/159 |
| 4,451,732 | 5/1984 | Spongr et al. | |
| 4,514,436 | 4/1985 | Moerschel | |
| 4,563,633 | 1/1986 | Johnson | 324/558 |
| 4,780,680 | 10/1988 | Reuter et al. | |
| 4,817,424 | 4/1989 | Pellatiro | |
| 4,862,065 | 8/1989 | Pazda | 324/558 |
| 4,865,872 | 9/1989 | Pellatiro | |
| 4,982,600 | 1/1991 | Kiso et al. | |
| 5,001,433 | 3/1991 | Osaki | |
| 5,014,547 | 5/1991 | Holroyd | 73/159 |
| 5,297,062 | 3/1994 | Cresson | 73/159 |

FOREIGN PATENT DOCUMENTS 0275685  12/1986  Japan ..................... 324/558

*Primary Examiner*—Kenneth A. Wieder
*Assistant Examiner*—Jose M. Solis
*Attorney, Agent, or Firm*—Haugen and Nikolai

[57] ABSTRACT

A detector for continuously monitoring the integrity of a coating on a piece of material. The detector includes an upper bar and a lower bar held near the surfaces of the material. Each bar carries multiple conductive probes in contact with the corresponding surface and electrically connected to an electronic detection circuit. Adjacent probes are connected to electric terminals having different voltage potentials. When probes from the same bar carrying different voltages short together, such as by contacting the surface of conductive sheet material, the detection circuit signals an insufficiently coated area has been found. The short between probes must be large enough to cause a short for more than a predetermined time. The upper probe bar is rotatable to prevent damage to the upper probes by a bent edge on a sheet of material.

18 Claims, 3 Drawing Sheets

COATING DEFECT DETECTOR SYSTEM

BACKGROUND OF THE INVENTION

I. Field of the Invention

This invention relates generally to material handling and inspection equipment and, more particularly, to a system for detecting an insufficient coating on coated metal sheet stock material.

II. Discussion of the Related Art

Sheet stock material is often laminated or coated with a layer of diverse composition to give it certain surface characteristics not found in the unprocessed material. Often, the stock material is inexpensive plastic or metal making up the bulk of a product and the coating is plastic for making the product safer or more appealing. Coating characteristics, such as electrical properties or chemical activity, or perhaps the look and feel of the coating, are often made to differ from those of the underlying material.

In the food container industry, and more specifically in the canned food industry, metal sheet stock is often used as the bulk material. The metal may be, for example, aluminum, steel or tin-plate converted into any size and shape container or lid. However, metal food containers must be coated to prevent contamination of the food inside the container and to prevent corrosion of the metal leading to failure of the container. The coating material is typically an enamel or lacquer paint. To provide an effective barrier, the enamel or lacquer coating must be continuous, i.e., must not contain voids or imperfections that permit the inner surface of the sheet stock to come into direct contact with food or the outer surface with the ambient environment. In addition, uncoated metal sheet stock is known to gall up the stamping dies used to form the containers. This increases the down time needed for cleaning dies and shortens die life significantly.

Detecting defects in the sheet material is preferably done before the bulk material is cut or formed into a specific product. For example, U.S. Pat. No. 3,188,478, issued to Binks, discloses an optical device for detecting pinholes in tin plate sheet material used to produce cans. Pinholes are typically very small and cannot be found by visual inspection. As the bulk sheet material passes through the detector, light from a source shining through a pinhole is used to actuate a photosensitive means which, in turn, causes a response in the form of a visible or audible signal. Of course, a device such as the one described by Binks cannot detect an insufficient coating on the surface of opaque sheet material.

In U.S. Pat. No. 3,759,095, Short, Jr. et al., describe a device for detecting surface flaws, such as cracks or splices, in a filmstrip. A mechanical feeler for sensing the surface of the film is attached to a piezoelectric crystal which moves in response to movement of the feeler. The piezoelectric crystal signals a circuit, which includes a capacitor for blocking gradually changing electric signals. Since only sudden changes in surface smoothness are detected, the device is not suited for detecting voids or insufficiently coated areas on a piece of sheet material. For example, the coating may be rough enough to give false positive signals or the transition from a coated portion to an uncoated portion may be smooth enough to produce no signal at all.

Devices and methods for measuring the thickness of a coating based on the electrical nature of the coating or based on the interaction of high energy radiation with the coating have also been described. U.S. Pat. No. 4,780,680, issued to Reuter et al., concerns an approach wherein the coating is charged by means of a corona and retained charge levels are measured by an electrostatic volt meter positioned downstream. These retained levels are then related to the thickness of the coating. U.S. Pat. No. 4,451,732 describes a very precise measuring system employing a radiation source and a Geiger-Muller Tube for detecting reflected radiation. Beta radiation is reflected from the coated sheet material and the intensity of the reflected radiation is measured to determine the thickness of the coating. However, radiating coated sheet material in the food container industry may not be acceptable and the precision available with this type of measurement is not needed.

Coating characteristics such as conductivity may also be measured directly and if the coating and the sheet material have different conductivities, a void or near void may be detected. U.S. Pat. No. 5,001,433, issued to Osaki, describes an apparatus and method for measuring the conductivity of material using a wave guide tube in which one end is connected to a transmitter for introducing a microwave and the other end open and directed toward the material. Either the reflected waves or the waves propagating through the material may be detected and measured to arrive at a determination of the conductivity.

Electrical conductivity is also measured by simply contacting the coated surface with multiple spaced contacts having different voltages and detecting and indicating shorts between contacts. It may also be configured to detect open circuit conditions, if desired. This type of device provides the necessary information at a cost which is typically below that of the radiation, corona charging or wave guide techniques.

One device employing this principle is an enamel void detector for can lines using coated sheet material produced by Opto-Mech, Inc. The Opto-Mech system includes a top and bottom roller each having 78 individual spaced detector rings. The rollers rotate as the sheet material passes between them and the rings float independent of adjacent rings to maintain contact with the sheet material. Every other ring is electrically connected together and also connected to a positive or a negative voltage such that adjacent rings have different potentials. The shorting of adjacent rings together through direct contact with metal sheet material, for example, indicates a void. Proximity switches sense the leading and trailing edges of the sheet material to prevent false triggering of the system due to uncoated edges. The electrical system uses brushes, such as carbon brushes, to provide contact between the rings and external electronics designed to compensate for changes in sensitivity; however, the brushes are prone to pick up dirt and dust from the sheet material and this may erode signals sent to the electronics.

The present invention solves problems associated with prior multiple spaced conductor type systems in a manner that increases reliability by enabling reduced sensitivity. The system enables conductivity probes to be wired directly to an electrical detection circuit and the detection circuit which may be relatively simple compared to those in other systems.

A principal object of the present invention is to provide a reliable system for detecting coating defects on a piece of coated sheet material of interest.

Another object of the invention is to provide a reliable system for detecting an insufficient coating on a piece of material of interest, based on detecting differences in conductivities between the material and the coating as detected by an electronic circuit.

Still another object of the invention is to provide an electrical system for detecting voids in a non-conductive coating on conductive sheet material that is relatively uncomplicated both mechanically and electrically.

A further object of the invention is to provide an improved system for detecting voids in a non-conductive coating on the surface of metal sheet material used in the fabrication of metal food containers.

A still further object of the invention is to provide an improved system for avoiding false signals due to uncoated edges of the material.

A yet still further object of the invention is to provide an improved system for detecting an insufficient coating on a sheet of material that also detects bent edges.

Other objects, features and advantages of the present invention will become apparent to those skilled in the art through familiarity with the specification, claims and drawings herein.

SUMMARY OF THE INVENTION

The foregoing objects of the present invention are attained by providing a system for continuously monitoring the integrity of a coating on a piece of passing sheet material that includes multiple spaced conductive probes held in contact with the surface of interest to be inspected. Individual linearly spaced probes are electrically connected to an electronic detection circuit which supplies different voltages to adjacent probes. In the embodiment of the detailed description, the electronic detection circuit is configured to detect shorts between probes having different voltages. However, detecting open circuit conditions between probes is also contemplated. The sheet material may be conductive material, such as aluminum, stainless steel or tin plate, and the coating may be a relatively non-conductive material, such as enamel or lacquer. Of course, the sheet material may be a partial conductor and the coating may be a partial insulator. The present invention requires only that the difference in conductivity be detectable by the electronic detection circuit such that the coating is seen as relatively non-conductive in comparison to the underlying material.

Mechanically, the probes are arranged in parallel spaced relation and securely attached to one or more bars positioned near and substantially parallel to the surface of interest. When sheet material is inspected, one bar may be positioned above the upper surface and a second bar positioned beneath the lower surface to detect voids on the corresponding surface and the material to be inspected caused to pass therebetween in strip or sheet form. Of course, if desired, only one bar may be used or only one bar connected to the electronic detection circuit.

In the preferred embodiment, a pair of bars are positioned to detect voids on upper and lower surfaces of a coated conductive sheet of material moving relative thereto. The lower or bottom probes are rigid conductors secured in the lower bar for detecting voids and also for supporting the sheet material as it passes relative to the detector. The upper or top probes are resilient, flexible conductors securely attached to the upper bar which is held substantially parallel to the upper surface of the sheet material transverse to the direction of relative displacement. The electronic detection circuit views each probe bar separately and for convenience a selector switch may be provided to permit sensing of one surface only for singly coated materials.

The electronic detection circuit includes an electronic relay which steps down a 120-volt AC signal to a 12-volt AC signal. The electronic relay supplies alternate probes with the two sides of the 12-volt signal and when the two sides are shorted together, the electronic relay opens. This identifies a poorly coated area on a passing sheet of material. A time delay relay is provided in the detection circuit for delaying the time between identifying a poorly coated area and sending a signal from the electronic detection circuit. By adjusting the time delay circuitry, false detections from bare edges may be ignored and bent edges, exposing more bare material, may be detected.

In the specific example of the detailed description, each probe bar carries a number of individual, spaced probes electrically connected to one side of the 12-volt AC signal. The probes may be connected to the voltage signals in any order and in the preferred embodiment, alternate probes are connected together to a common side. Thus, for example, odd numbered probes might carry the positive or hot signal and even numbered probes might carry the negative or return signal.

In operation, a relatively low impedance, conductive sheet of material coated with a high impedance, relatively non-conductive coating is advanced between upper and lower drive rollers and addressed by the lower rigid wires and the upper resilient wires. The drive rollers may be synchronously driven at the same speed as sequential conveyors in a sheet material processing system to maintain a consistent line speed for producing products. The lower rigid wires support the sheet material and detect voids or poor coverage on the lower surface and the upper resilient wires detect voids or poor coverage on the upper surface.

When probes having different instantaneous voltages are shorted together through the surface of the conductive material for a predetermined time, the electronic detection circuit signals a programmable logic controller in the sheet material processing system which may then avoid the insufficiently coated area or the piece of sheet material having the void may be removed. A fault reset button is provided to reset the electronic detection circuit to resume system operation.

The apparatus of the present invention will detect a bent edge on a sheet of material. A bent edge exposes the bare edge to the probes for a longer period of time than a straight edge. Thus, a bent edge is detected by adjusting the predetermined time delay required between shorting of the probes and sending a signal from the detection circuit. The upper probe bar is free to rotate parallel to the upper surface to move the probes up and avoid damage from a bent edge. A spring biased collar firmly attached to the upper probe bar urges the upper probes into contact with the upper surface.

DETAILED DESCRIPTION

Figure 1:
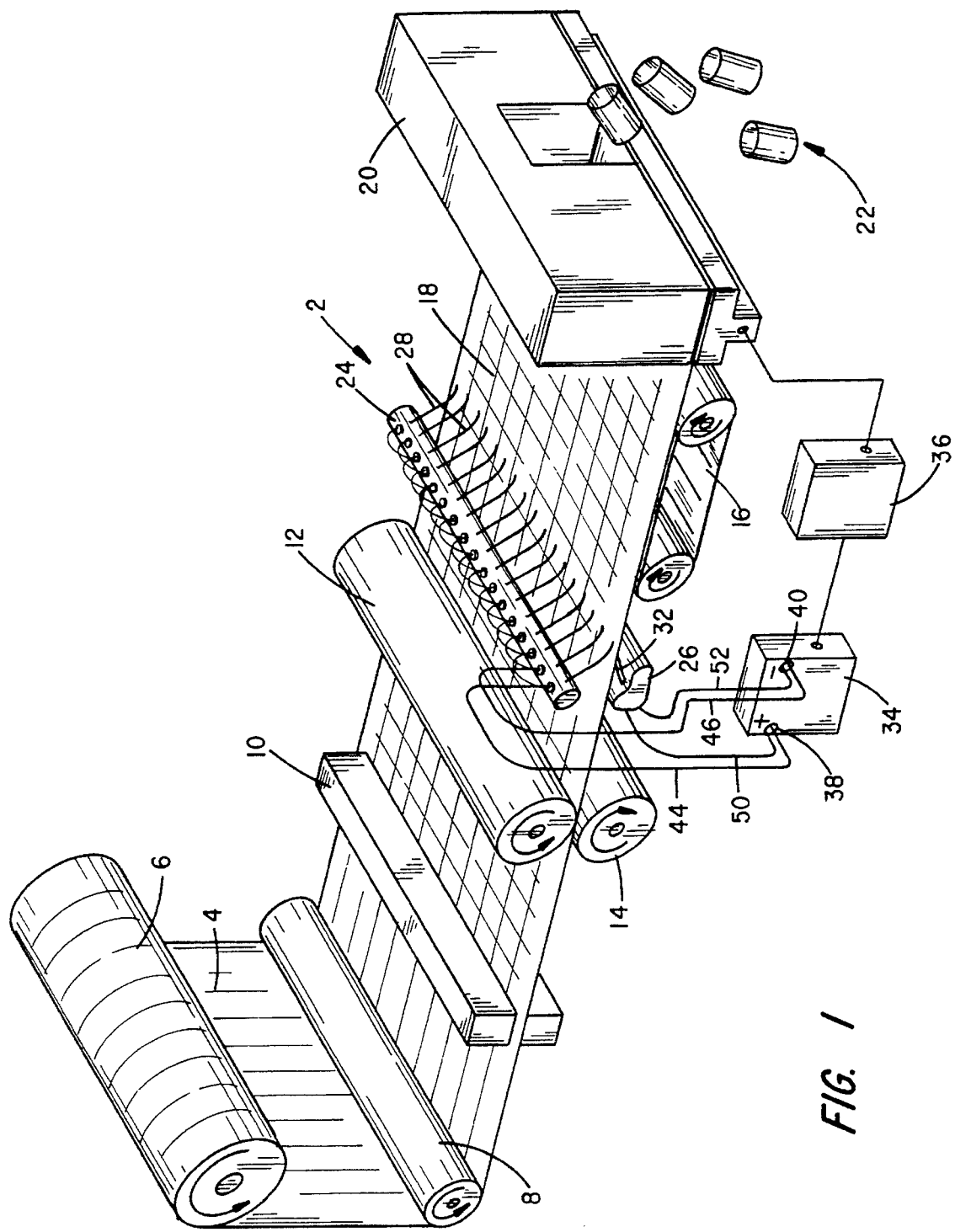
FIG. 1 is a schematic side view of a sheet material processing system employing the present invention.

As shown in FIG. 1, the detector of the present invention, indicated generally by the reference numeral 2, may be employed in a sheet material processing system. In this system, sheet material 4 is supplied as a continuous web or strip from a roll 6, or as individual sheets (not shown), and conducted around guide roller 8 through coating device 10 by driven rollers 12 and 14 at a speed corresponding to the speed of the processing system conveyor belt 16. The web of sheet stock material 4 is coated on either or both upper and lower surfaces in a well known manner and the detector 2 thereafter checks for voids in the coating. The coated sheet material 18 continues down the line after inspection for further processing, i.e., cutting and shaping such as by a shearing machine, a punch press or a stamping machine 20 to produce cans 22. Of course, any number of other steps or inspection devices may be employed in the manufacturing line either prior to or after the cans are formed and the concepts of the present invention may be applied to detect insufficiently coated areas on material previously formed into curvilinear, rectangular or other shapes.

Figure 2:
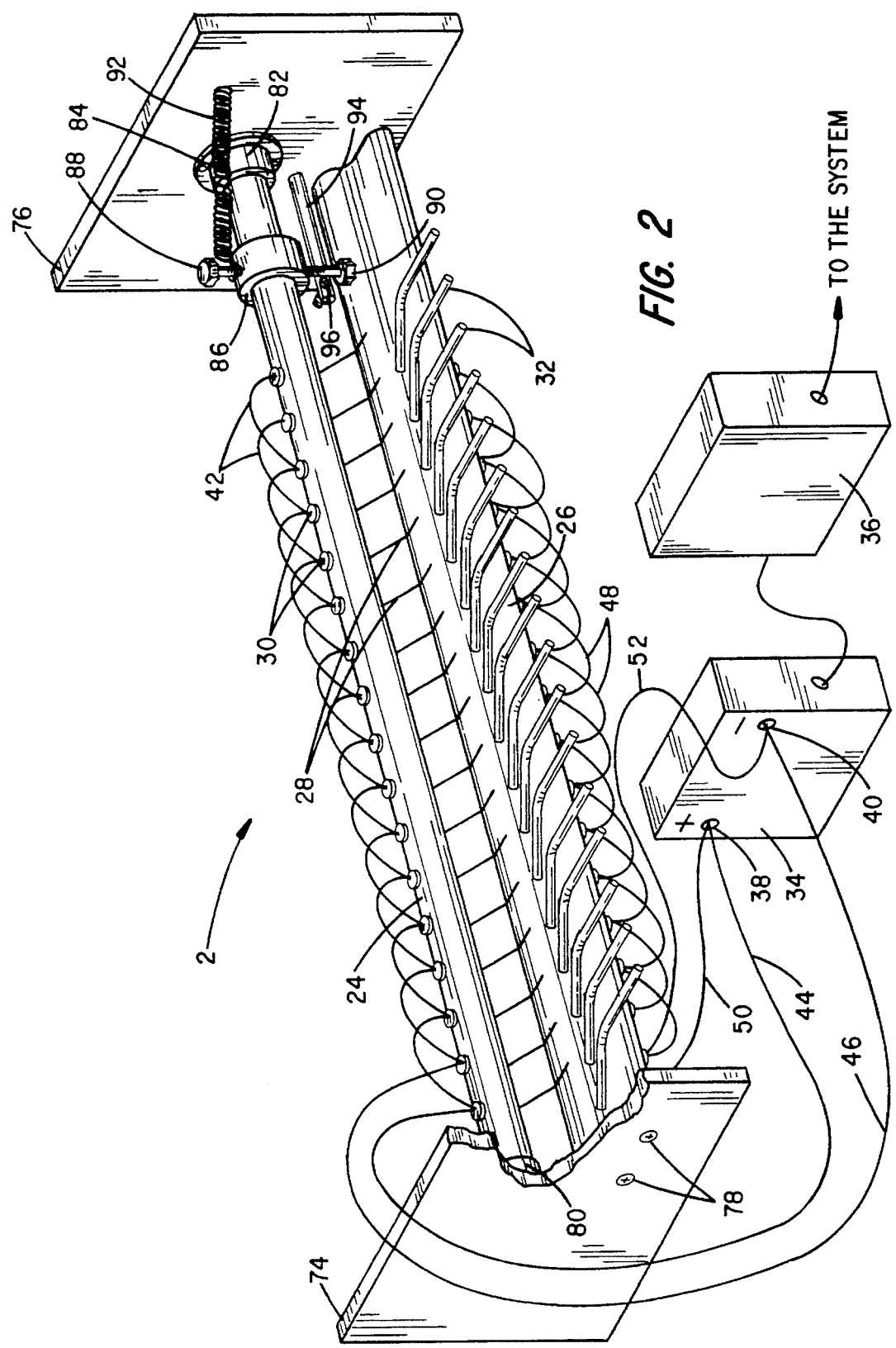
FIG. 2 is a schematic perspective view of a bare sheet detector for practicing the concepts of the present invention.

The inspection system 2, as shown in FIGS. 1 and 2, includes an upper bar 24 and a lower non-revolving bar 26 held in place above and below the coated sheet material 18. The bars 24 and 26 are made from a rigid non-conductive material which may be a high impact plastic such as a polyamide. In one successful embodiment, Nylon 6/6 was used. The upper bar 24 carries upper resilient conductive probes 28 securely attached thereto as by screws 30 and held in contact with the coated sheet material 18. In the specific example of the detailed description, the resilient conductive probes 28 are piano wire 0.02 inches (0.05 cm) in diameter. Lower rigid conductive probes 32 are held in precisely drilled holes in the lower bar 26 as by screws (not shown) and in the embodiment of the detailed description, the lower conductive probes 32 are made from stainless steel 0.06 inches (0.15 cm) in diameter. The lower conductive probes 32 must be rigid enough to properly support the coated sheet material 18 as it passes between the upper and lower bars 24 and 26.

An electronic detection circuit 34 is provided electrically connected to the upper and lower conductive probes 28 and 32. The detection circuit 34 responds to signals from the upper and lower probes 28 and 32 by signaling process control mechanism 36. In one embodiment, the control mechanism 36 is a programmable logic controller which signals the downstream punch press or other forming device 20 to stop, or otherwise not use material containing a void. In another embodiment, the programmable logic controller or control mechanism 36 stops the entire line so an individual sheet of material having a void may be removed and replaced with a sheet having a good coating to preserve continuity in the line.

Upper and lower conductive probes 28 and 32 are electrically connected to either a hot (positive) terminal 38 or a return (neutral or negative) terminal 40 on detection circuit 34. In the embodiment of the detailed description, alternate upper probes 28 are connected together by wires 42 to form two ganged sets of probes. One set is connected to the hot terminal 38 by wire 44 and the other is connected to the return terminal 40 by wire 46. Similarly, alternate lower probes 32 are connected together by wires 48 to form two sets of ganged probes with one set connected to hot terminal 40 by wire 50 and the other connected to return terminal 40 by wire 52. Thus, adjacent probes carry different voltages. In another embodiment of the invention, the conductive probes 28 and 32 may be connected to terminals 38 and 40 in a different configuration, such that adjacent probes are not connected to different voltages.

The electronic detection circuit 34 may be configured to detect both shorts and open circuit conditions between probes. In the embodiment of the detailed description, the detection circuit 34 is configured to distinguish a short from an open circuit condition. The sheet material of interest may be only a partial (relatively high impedance) conductor and the coating may be only a partial insulator. The present invention requires only that the difference in conductivity be detectable by the detection circuit 34 such that the coating is perceived as a different impedance material than the underlying sheet material 4.

Figure 3:
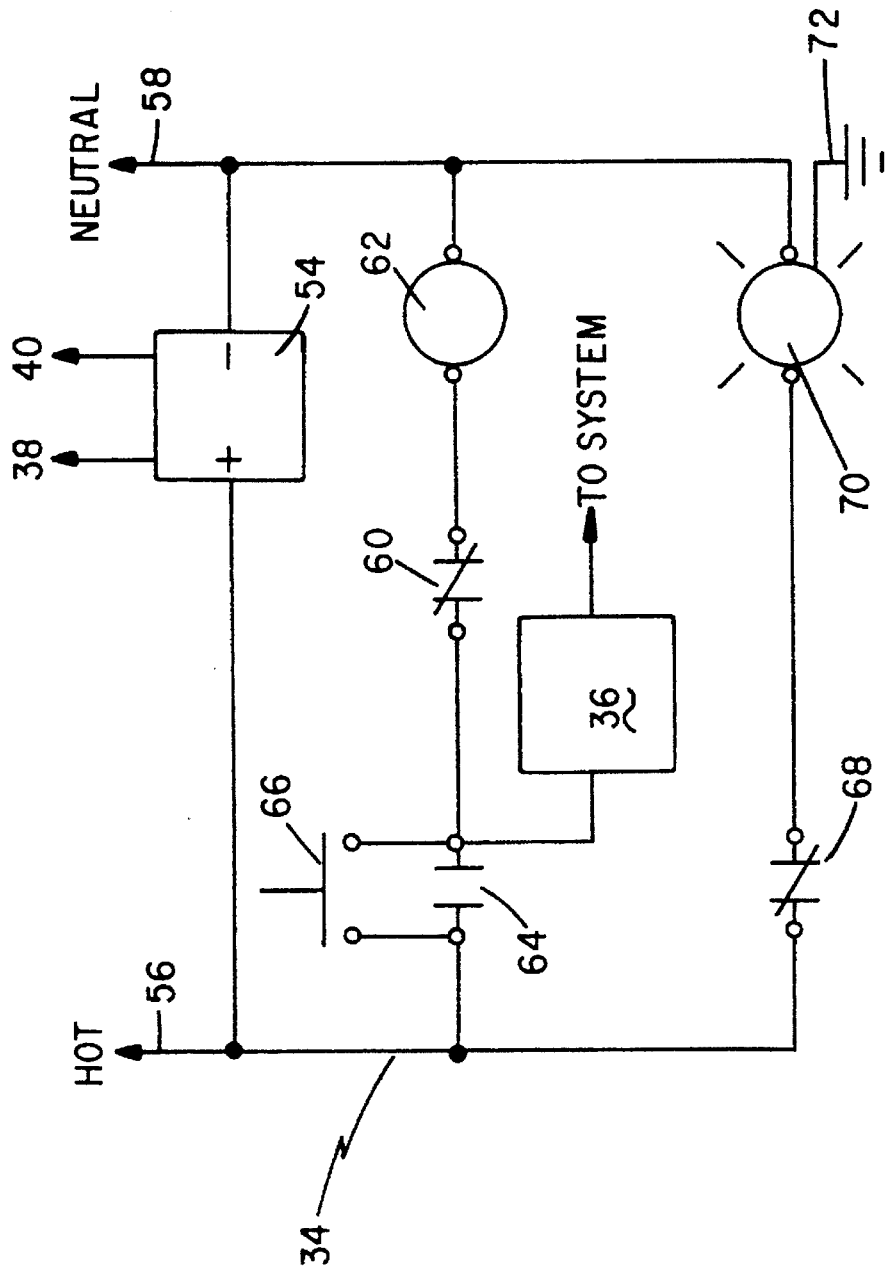
FIG. 3 is an electrical schematic of an electronic detection circuit of the preferred embodiment.

As shown in FIG. 3, the detection circuit 34 has an electronic relay 54 provided with a hot (positive) terminal 38 and a return (negative) terminal 40. Hot wire 56 is connected to one side of electronic relay 54 and neutral wire 58 is connected to the other side. Electronic relay 54 steps down the 120 volt AC signal between hot wire 56 and neutral wire 58 to a 12 volt AC signal between hot terminal 38 and return terminal 40. Thus, upper and lower probes 28 and 32 receive a 12-volt AC signal from terminals 38 and 40. Electronic relay 54 is provided with normally closed (NC) contacts 60 which open when terminals 38 and 40 are shorted together. NC contacts 60 are connected in series with a timing relay coil 62 and normally open (NO) timing relay contacts 64. A fault reset button 66, for resetting the timing relay, is provided in parallel with NO timing relay contacts 64. Depressing the fault reset button 66 shorts the circuit across timing relay contacts 64 to allow current to flow through NC contacts 60 and timing relay coil 62. This closes NO timing relay contacts 64 and current flows from hot wire 56 through contacts 64 and 60 to timing relay coil 62 and neutral wire 58. Timing relay 62 has associated NC contacts 68 electrically connected on one side to hot wire 56 and on the other side to an indicator light 70, which, in turn, is connected to neutral wire 58 and ground 72. When current flows through timing relay coil 62, NC contacts 68 are open and indicator light 70 is off.

In operation, when probes on one bar 24 or 26 having different voltages contact an insufficiently coated area, terminals 38 and 40 short together and electronic relay NC contacts 60 open. If the detection circuit 34 has been reset, opening NC contacts 60 prevents current from flowing through timing relay coil 62. This opens timing relay contacts 64 after a predetermined delay time period times out. The delay time period may be adjusted to a setting between, for example, 10 milliseconds (ms) and 100 ms. This allows adjustment of the sensitivity of the system to prevent such things as false indications given by, for example, uncoated edges on the coated sheet material 18 from stopping the sheet material processing system. The opening of timing relay contacts 64, of course, disconnects hot wire 56 from controller 34. This may be implemented to stop the system or, for example, preventing the punch press 20 from stamping a container from the insufficiently coated area. As NO timing relay contacts 64 open, NC timing relay contacts 68 close to complete the circuit between hot wire 56 and trouble indicator light 70. This provides a visual indication that a fault has occurred. Reset button 66 is pushed to reset the system.

In another aspect of the present invention, shown in FIG. 2, upper bar 24 and lower bar 26 are held in place by left and right support members 74 and 76. Lower bar 26 is securely attached to support members 74 and 76, such as with screws 78. However, upper bar 24 is rotatably held in place, its ends journalled in flanged bearings 80 and 82, which, in turn, are securely attached to support members 74 and 76, such as with screws 84. The probes 28 are urged into contact with the coated sheet material 18 by spring biased collar 86 securely attached to upper bar 24 as by collar screws 88 and 90. Collar screw 88 has an attached biasing spring 92 which is also attached to support member 76. Collar 86 and spring 92 operate to rotate bar 24 and urge probes 28 into contact with the coated sheet material 18. A collar stop 94 is provided securely attached to support member 76 and acts with set screw 96 to provide a positive stop for the rotation of the bar 24. Set screw 96 is preferably set to bring probes 28 in proper tension with the sheet material. Upper bar 24 rotates to move probes 28 up to avoid damage if a bent sheet of material passes through the detector 2. To detect a bent edge, the predetermined time delay is set sufficiently long to ignore the bare edge on a straight piece of material but short enough to detect a larger bare area on a bent sheet. This prevents sheet material having a bent edge greater than a predetermined amount from moving through the material processing system and damaging components at a later stage.

The invention has been described herein in considerable detail in order to comply with the Patent Statues and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention.

What is claimed is:

1. An apparatus for detecting imperfections, including voids in a high impedance coating on a moving sheet of conductive material having first and second generally parallel planar surfaces, said apparatus comprising:

(a) a first elongated transverse member held generally in spaced parallel relation to the first planar surface of the coated sheet of material;

(b) a second elongated transverse member held generally in spaced parallel relation to the second planar surface of the coated sheet of material;

(c) a first set of spaced generally parallel electrical contact elements arranged along and carried by said first transverse member for contacting said first planar surface;

(d) a second set of spaced generally parallel electrical contact elements arranged along and carried by said second transverse member for contacting said second planar surface;

(e) resilient biasing means attached to said first and said second transverse members for urging said first and said second sets of spaced contact elements into contact with said first and said second planar surfaces of the coated sheet of material as it moves relative thereto;

(f) sources of unequal electric potential connected to supply electrical potential to each of said first and said second sets of spaced conductors in a manner such that adjacent conductors in each of said first and second sets of spaced conductors carry different voltage potentials; and (g) detection means connected to said first and second sets of contact elements for detecting differences in impedance in the high impedance coating on both the first and second planar surfaces of the coated sheet of material based on conduction between conductors of different potential in each of said first and said second sets of spaced conductors.

2. The apparatus of claim 1 wherein said contact elements of said first and second sets are elongated resilient elements.

3. The apparatus of claim 1 including means for rotating at least one of said first and second transverse members thereby moving corresponding one or more sets of contact members from contact with said moving sheet of conductive material.

4. The apparatus of claim 1 further comprising programmable control means for controlling a different device based on detection of an imperfection in said moving sheet of conductive material.

5. The apparatus of claim 1 further comprising means for regulating the sensitivity of said detection means.

6. The apparatus of claim 1 wherein said detection means further comprises time delay means to preclude sheet edges from being detected as imperfections.

7. The apparatus of claim 4 wherein said detection means further comprises time delay means to preclude sheet edges from being detected as imperfections.

8. The apparatus of claim 7 wherein said electrical contact elements are elongated resilient elements.

9. The apparatus of claim 1 further comprising means for detecting a bend in said sheet of conductive material.

10. An apparatus for detecting imperfections including voids in a high impedance coating on a moving sheet of conductive material having first and second generally parallel planar surfaces, said apparatus comprising:

(a) a first elongated rigid transverse member held generally in spaced parallel relation to the first planar surface of the coated sheet of material;

(b) a second elongated rigid transverse member held generally in spaced parallel relation to the second planar surface of the coated sheet of material;

(c) a first set of spaced generally parallel electrical contact elements arranged along and carried by said first transverse member for contacting said first planar surface;

(d) a second set of spaced generally parallel electrical contact elements arranged along and carried by said second transverse member for contacting the second planar surface and supporting said coated sheet;

(e) resilient biasing means attached to said first transverse member for urging said first set of spaced contact elements into contact with said first planar surface of the coated sheet of material as it moves relative thereto;

(f) sources of unequal electric potential connected to supply electrical potential to each of said first and said second sets of spaced conductors in a manner such that adjacent conductors in each of said first and second sets of spaced conductors carry different voltage potential; and (g) detection means connected to said first and second sets of contact elements for detecting differences in impedance in the high impedance coating on both the first and second planar surfaces of the coated sheet of material based on conduction between conductors of different potential in each of said first and said second sets of spaced conductors.

11. The apparatus of claim 10 wherein said contact elements of said first set are elongated resilient elements.

12. The apparatus of claim 10 including means for rotating said first transverse member thereby moving corresponding contact members from contact with said moving sheet of conductive material.

13. The apparatus of claim 10 further comprising programmable control means for controlling a different device based on detection of an imperfection in said moving sheet of conductive material.

14. The apparatus of claim 10 further comprising means for regulating the sensitivity of said detection means.

15. The apparatus of claim 10 wherein said detection means further comprises time delay means to preclude sheet edges from being detected as imperfections.

16. The apparatus of claim 13 wherein said detection means further comprises time delay means to preclude sheet edges from being detected as imperfections.

17. The apparatus of claim 10 further comprising means for detecting a bend in said sheet of conductive material.

18. The apparatus of claim 1 wherein said change in impedance detected is a drop in impedance.

* * * * *